(12) United States Patent
Truitt et al.

(10) Patent No.: US 8,636,720 B2
(45) Date of Patent: Jan. 28, 2014

(54) NEEDLELESS ACCESS CONNECTORS AND VALVE ELEMENTS THEREFOR

(75) Inventors: Tim L. Truitt, Orange, CA (US); Alex T. Mazza, Grand Terrace, CA (US)

(73) Assignee: CareFusion 303, Inc., San Diego, CA (US)

( * ) Notice: Subject to any disclaimer, the term of this patent is extended or adjusted under 35 U.S.C. 154(b) by 559 days.

(21) Appl. No.: 12/619,598

(22) Filed: Nov. 16, 2009

(65) Prior Publication Data

US 2012/0310179 A1  Dec. 6, 2012

(51) Int. Cl.
*A61M 25/16*  (2006.01)

(52) U.S. Cl.
USPC ........................................ 604/537; 251/149.1

(58) Field of Classification Search
USPC ............... 604/256, 533–539, 905; 251/149.1, 251/149.3, 149.6, 149.7
See application file for complete search history.

(56) References Cited

U.S. PATENT DOCUMENTS

| | | | | |
|---|---|---|---|---|
| 5,730,418 A | * | 3/1998 | Feith et al. | 251/149.6 |
| 2006/0089603 A1 | | 4/2006 | Truitt et al. | |
| 2006/0163515 A1 | | 7/2006 | Ruschke | |

FOREIGN PATENT DOCUMENTS

WO  WO 2007/008511  1/2007

OTHER PUBLICATIONS

Max Plus Brochure, http://www.maximusmedical.com/pdf/maxPlus_Brochure.pdf (last accessed Jul. 29, 2009), 2 pages, Medegen, Inc.
Max Plus Clear Brochure, http://www.maximusmedical.com/pdf/MaxPlusClearNewFlyer.pdf (last accessed Jul. 29, 2009), 2 pages, Medegen, Inc.
Garcia, R. et al., "A Study of the Effects on Bacteremia and Sharps Injury Rates after Introduction of an Advanced Luer Activated Device (LAD) for Intravascular Access in a Large Hospital Setting," http://www.maximusmedical.com/pdf/Garcia%20Study.pdf (last accessed Jul. 29, 2009), 6 pages, Medegen, Inc.
International Search Report and Written Opinion dated Mar. 24, 2011 for PCT/US2010/056749.

* cited by examiner

*Primary Examiner* — Kami A Bosworth
(74) *Attorney, Agent, or Firm* — McDermott Will & Emery LLP

(57) ABSTRACT

A collapsible valve for use in a needleless access connector to reduce the priming volume of the needleless access connector. A needleless access connector with a small priming volume. A method of connecting a first medical device to a second medical device with a needleless access connector with a small priming volume.

9 Claims, 8 Drawing Sheets

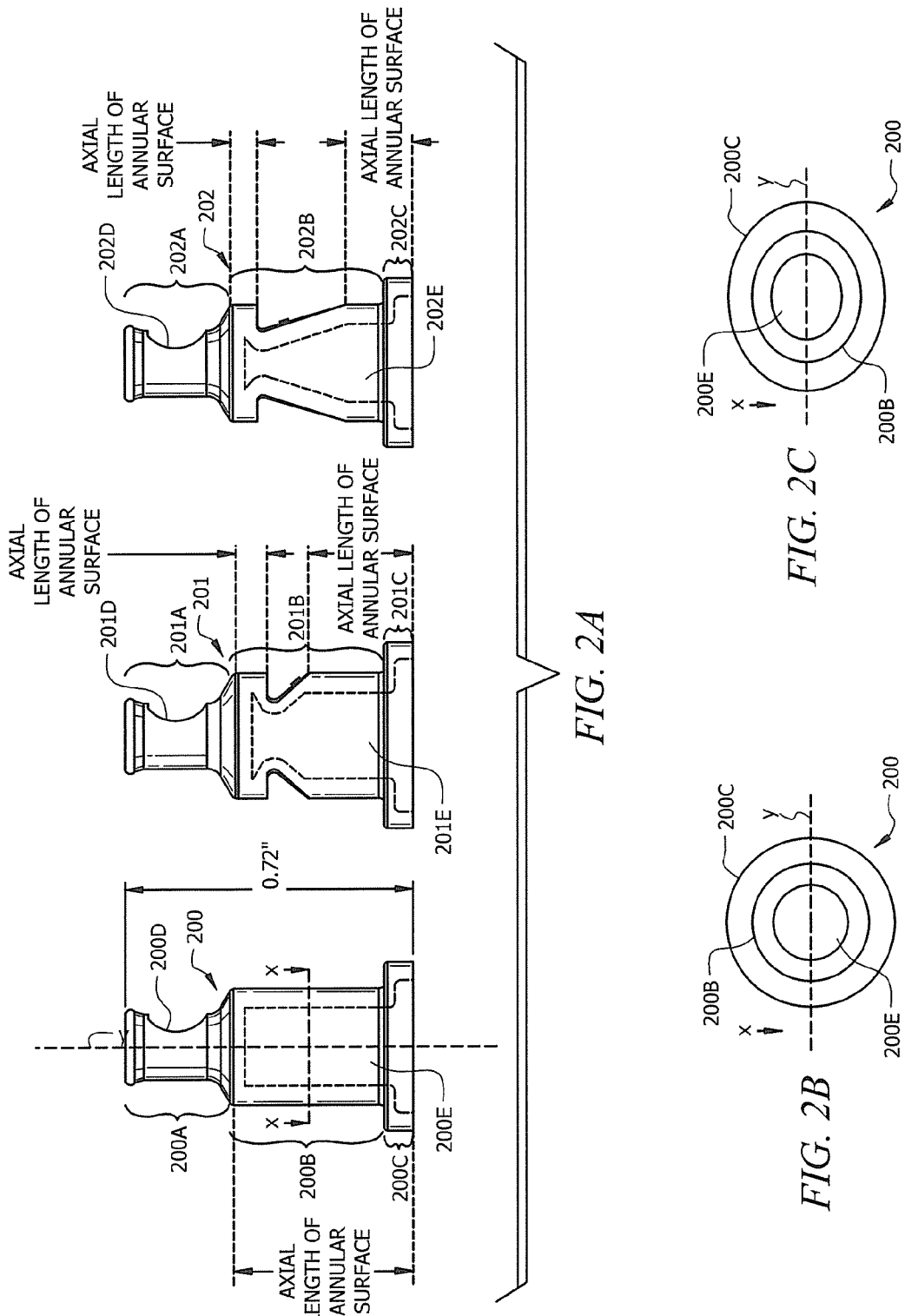

NEEDLELESS ACCESS CONNECTORS AND VALVE ELEMENTS THEREFOR

TECHNICAL FIELD

This disclosure relates to needleless access connectors and more particularly to positive displacement needleless access connectors that have a small priming volume.

BACKGROUND OF THE INVENTION

Modern medical treatment often requires medical professionals to introduce fluids into a patient or withdraw fluids from a patient. For example, a patient may need treatment that requires a medical professional to withdraw urine or blood from the urethra or a vein, respectively. Conversely, the medical professional may need to introduce drugs or nutrients into the patient's vein (i.e., intravenously). To create a path for the flow of fluid into or from the patient, one method requires that the medical practitioner use a catheter where one end of the catheter is inserted into the patient. The other end of the catheter connects to an intravenous bag (IV bag), through an IV line. Needleless access connectors employ valves that allow a medical practitioner to remove or add devices (e.g., IV bags) to the catheter without the use of a needle. An example of a needleless access connector is shown in FIGS. 1A and 1B.

FIG. 1A is a cut-away view of a current needleless access connector 100. Needleless access connector 100 includes female luer fitting 101, male luer fitting 102, and valve 103. When in use, male luer fitting 102 is connected to, e.g., a catheter or to a female luer, and female luer fitting 101 is connected to a fluid reservoir, e.g., an IV bag or male luer. Female luer fitting 101 is connected to the fluid reservoir via a second male luer fitting 106, which has a hollow member (as shown in FIG. 1B) and is inserted through the top of female luer fitting 101. The insertion of male luer 106 collapses valve 103 down into volume 104 to break the seal and create a fluid flow path. FIG. 1B shows collapsible valve 103 in the collapsed position after insertion of male luer 106 into female luer 101. Male luer 106 delivers fluid, e.g., from an IV bag, which flows around valve 103 into channels in male luer fitting 102 and into the catheter or female luer.

Inside valve 103 is a gap (or septum, not shown), that is filled with air. Needleless access connector 100 is a positive displacement device, so that when a new connection is made at female luer fitting 101, device 100 pulls fluid in from the male side of the valve (i.e., the side proximate male luer fitting 102). When a disconnection is made at female luer fitting 101, device 100 pushes fluid in from the female side (i.e., the side proximate the top of female luer fitting 101). The advantage of positive displacement is that when a disconnection is made, device 100 expels fluid out of the male luer fitting 102 and effectively flushes the catheter. By contrast, some devices on the market today have negative displacement, so that when a male luer (e.g., male luer 106) is disconnected, such devices pull a small amount of liquid from the male luer 102 side. When liquid is pulled from the male luer 102 side of a catheter that is attached to the vein of a patient, blood could be pulled into the catheter lumen and if this blood is left in the catheter lumen it may clot and cause health problems for the patient. Positive displacement connectors avoid this problem by pushing fluid out when a male luer (e.g., male luer 106) is disconnected from the needleless access connector and its collapsible valve moves from its collapsed state to its uncollapsed state. The purging of fluid, from positive displacement connectors, helps to prevent blood from entering the tip of the catheter, thereby preventing blood clotting/contamination and thus, bloodstream infections.

In operation, when the female end of needleless access connector 100 is accessed by a male luer (FIG. 1B), valve 103 is sufficiently elastic so that it can bend out of the way to allow flow and then return to its original shape after a disconnection is made at the female end. Thus, needleless access connector 100 re-seals itself and forms a flat surface that can be disinfected at the top surface 110 using an alcohol swab.

Needleless access connector 100 has a partially annular valve body because it has weakness points on both sides by virtue of duckbills 105. Duckbills 105 encourage the collapse of collapsible valve 103. Furthermore, needleless access connector 100 includes uniform wall thickness in the valve body, even at and around duckbills 105.

Before needleless access connector 100 is used to connect a device to, for example a catheter, needleless access connector 100 will contain some air. This air is removed before using needleless access connector 100 with a catheter because otherwise it may be pumped into the patient causing harm to the patient. Usually, to remove this air, the medical practitioner inverts the needleless access connector and attaches a syringe containing saline to the needleless access connector. The saline is then pushed through the needleless access connector, thereby expelling the air from the connector. (This process is known as priming, and the minimum volume of liquid required to remove all the air from the needleless access connector is known as the priming volume.) Some medical practitioners prefer needleless access connectors with smaller priming volumes to reduce delay in medication delivery.

After a needleless access connector is primed, the medical practitioner usually connects the male end 102 to a catheter (not shown) The medical practitioner connects a male luer from the IV bag (not shown) to the needleless access connector. For example, a medical practitioner would connect the end of syringe 106 to female luer fitting 101, as shown in FIG. 1B.

The preferences of medical practitioners, discussed above regarding needleless access connectors, are significant especially in view of the fact that some of these medical practitioners, such as nurses, have to perform connecting of needleless access connectors many times during the course of a day.

BRIEF SUMMARY OF THE INVENTION

The present disclosure is directed to positive displacement needleless access connectors that have a small priming volume. One embodiment of the invention is a collapsible valve for use in a needleless access connector. The collapsible valve includes a first portion with at least one smiley cut in a section of this first portion. The collapsible valve has a length of 0.62 to 0.82 inches. Further, the collapsible valve is adapted to provide positive displacement. Another embodiment of the invention is a positive displacement needleless access connector that includes a housing and a collapsible valve disposed in the housing. The collapsible valve has a length of 0.62 to 0.82 inches. An apparatus according to one embodiment of the invention is a positive displacement needleless access connector that includes a housing and a collapsible valve disposed in the housing. The housing and the valve cooperate so that a volume of liquid required to expel air from the needleless access connector is about 0.17 to 0.19 milliliters.

Another embodiment of the invention is a positive displacement needleless access connector that includes a housing and a collapsible valve disposed in the housing. A method according to one embodiment of the invention is for connecting a first medical device to a second medical device with a needleless access connector. The method includes inserting a male luer of the needleless access connector into the female luer of the second medical device. The method further includes inserting a male luer section of the first medical device into a female luer of the needleless access connector. The needleless access connector is a positive displacement needleless access connector that includes a housing and a collapsible valve disposed in the housing. The collapsible valve has a length of 0.62 to 0.82 inches.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIG. 2A shows three exemplary collapsible valves used in tests of needleless access connectors;

FIGS. 2B-2C are cut-away, top-down views of different exemplary configurations of a valve according to embodiments of the invention;

DETAILED DESCRIPTION OF THE INVENTION

Figure 1A:
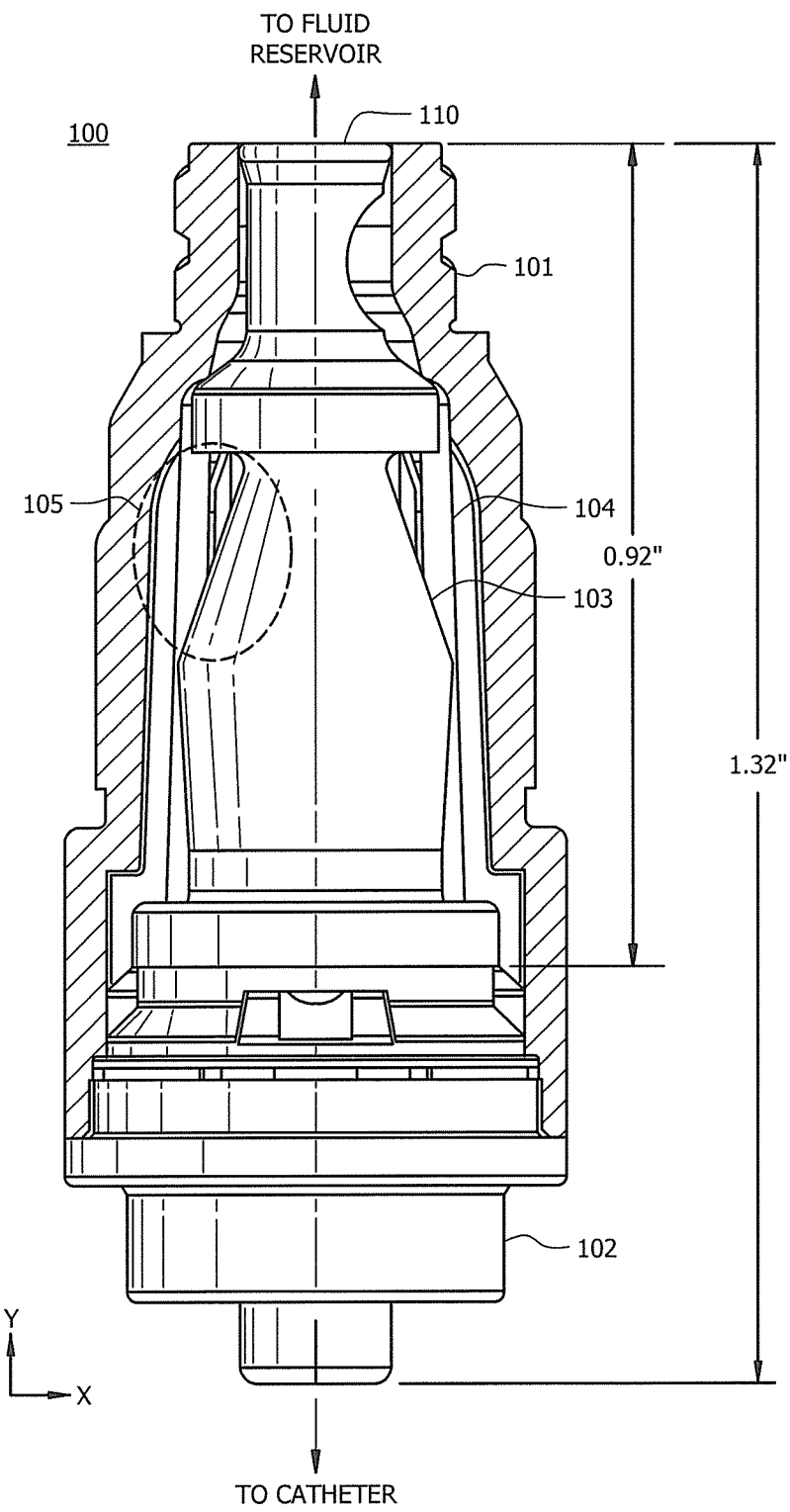
FIGS. 1A and 1B are cut-away views of a prior art needleless access connector.

To address the issues of reducing priming volume, different configurations of valves for needleless access connectors are disclosed. Tests were performed to establish operability and priming volume for each positive displacement needleless access connector. Priming volume is the minimum volume of liquid used to purge air from the needleless access connector. The tests were conducted on three needleless access connectors each containing different collapsible valves. The configurations of the three different collapsible valves are shown in FIG. 2A. It was observed that the amount and size of the duckbills, which are known in the prior art as being an important part of some collapsible valves, and the reduction in length of the collapsible valve, as compared to prior art valves, affects priming volume of a needleless access connector.

In one test where the duckbills were completely removed from the collapsible valve (valve 200) and the valve was reduced to 0.72 inches from a typical length of a prior art valve of 0.92 inches, it was observed that the priming volume for this valve was lower than the two other valves—valve 201, which had small duckbills and valve 202, which had large duckbills. It should be noted that reducing the compressible valve length from 0.92 inches to 0.72 inches allows for the reduction in total device length from 1.32 inches to 1.12 inches. Some test results are shown in TABLE I below.

TABLE I

|  | Illustration in FIG. 2A | Priming volume (milliliters) |
| --- | --- | --- |
| Cylindrical Valve | 200 | 0.175 |
| Small Duck Bill Valve | 201 | 0.187 |
| Large Duck Bill Valve | 202 | 0.204 |

The results of the tests indicate that the priming volumes of needleless access connectors that employ the configuration of valve 200—miniaturized collapsible valves with a significant portion of the outside surface being annular—may have a priming volume of around 0.175 milliliters and concomitantly allow good flow rates, though various embodiments may have different priming volumes. For example, the priming volume may range from 0.17 to 0.19 milliliters.

Different configurations of collapsible valve 200 may have an annular outside surface. For example, collapsible valve 200 includes first portion 200A, second portion 200B and third portion 200C. First portion 200A does not have a significant annular outside surface because it has a smiley cut 200D interrupting the annular characteristic. In contrast, second portion 200B and third portion 200C both have annular outside surfaces. FIG. 2B shows second portion 200B cut in a plane, x, perpendicular to plane y. The annular outside surface shown in FIG. 2B relative to plane y is circular. FIG. 2C shows another possible annular outside surface. It should be noted that the axial length of the annular outside surface does not include portions of the outside surface with collapse assistance structures such as smiley cuts and duckbills. For instance, collapsible valve 201 has less axial length of its annular surface than does collapsible valve 200 by virtue of the duckbills on second portion 201B which interrupt the annular characteristic. Collapsible valve 202 has even less axial length of its annular surface by virtue of its duckbills that dominate second portion 202B.

FIG. 2A illustrates exemplary embodiments of the invention. Collapsible valves 200 to 202 are miniaturized valves that may be used in a needleless access connector. Collapsible valves 200 to 202 have smiley cuts, 200D to 202D in first portions 200A to 202A, respectively. Collapsible valves 200 to 202 have a height (axial length) of 0.72 inches but may be within the range of 0.62 to 0.82 inches in various embodiments. Collapsible valves 200 to 202 are adapted to provide positive displacement, in part, by virtue of voids 200E to 202E. Before the needleless access connectors, in which collapsible valves 200 to 202 are installed, are put in use, voids 200E to 202E contain air.

FIG. 2A illustrates that, in various embodiments of the invention, the annular portion of the outside surface of the collapsible valve spans about 30% to 66% of the total axial length of the collapsible valve. Collapsible valves 200 to 202 have a total axial length of 0.72 inches. The amount of axial length of the annular surface varies amongst valves 200 to 202 by virtue of the amount and size of the collapse assistance structures present in each of these valves. Each of these valves has smiley cuts in first portions 200A to 202A that cause a portion of the axial length of valves 200 to 202 not to have an annular outside surface. In other words, the axial length of first portions 200A to 202A does not have an annular outside surface. First portions 200A to 202A have an axial length of about 0.25 inches or about 34% of the total axial length of valves 200 to 202. Thus, at least 34% of the axial lengths of valves 200 to 202 do not have an annular outside surface because of smiley cuts 200D to 202D.

Considering valve 200, second portion 200B and third portion 200C have annular outside surfaces. These annular portions represent the other 66% of the axial length of valve 200 (apart from first portion 200A) that has an annular outside surface. Specifically, second portion 200B has an axial length of about 0.4 inches or about 56% of the total axial length of valve 200. Third portion 200C has an axial length of about 0.07 inches or about 10% of the total axial length of valve 200.

Collapsible valves 201 and 202 have even less outside annular surface than collapsible valve 200 because of the duckbills in second portions 201B and 202B. Collapsible valve 202 for example, with the larger duckbills, may have an annular outside surface that spans about 30% of the axial length of valve 202 (i.e., 20% provided from second portion 202B and 10% provided by third portion 202C).

Figure 3A:
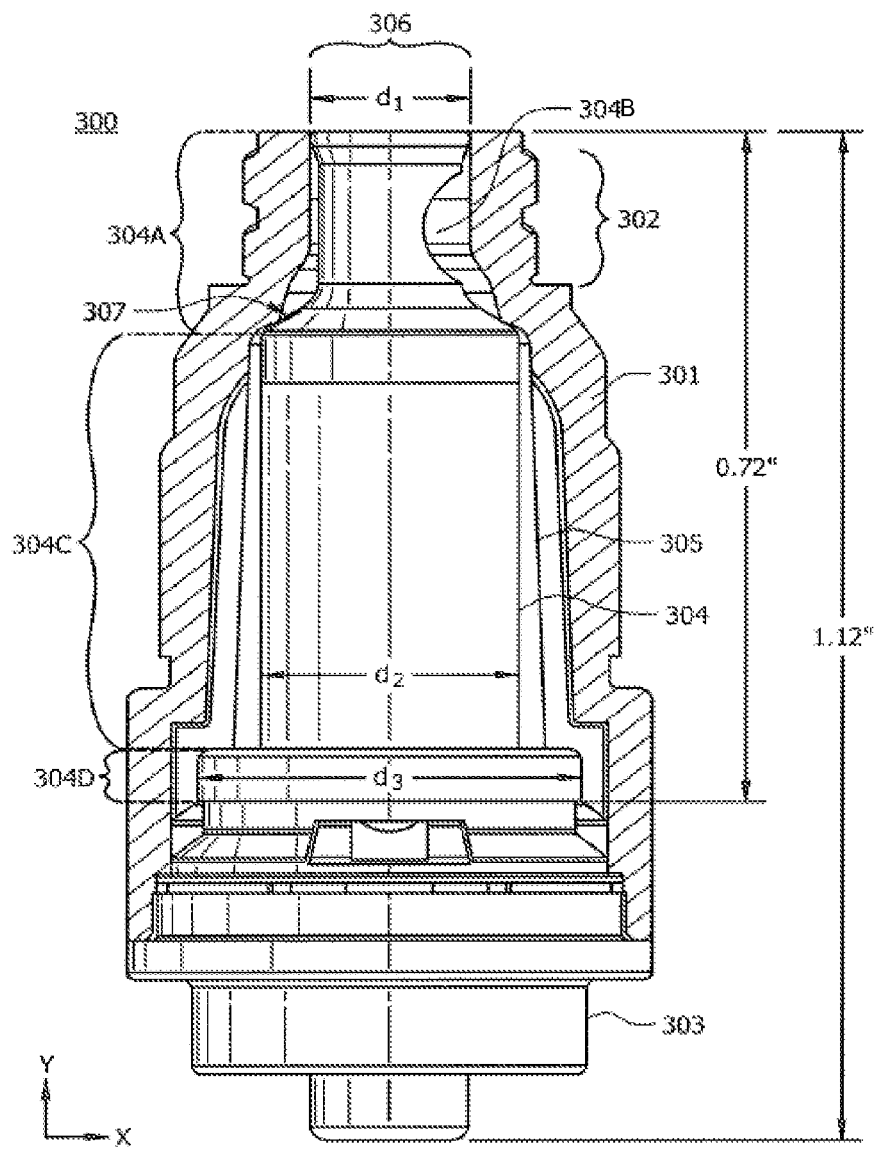
FIGS. 3A and 3B illustrate different views of an exemplary needleless access connector according to one embodiment of the invention.

FIG. 3A is a cut-away view of exemplary needleless access connector 300 according to one embodiment of the invention. Needleless access connector 300 includes housing 301. Housing 301 may be made of material including polycarbonate, polystyrene and acrylonitrile butadiene styrene. Housing 301 comprises top threaded part 302. It should be noted that the configuration of top threaded part 302, in some embodiments, meets ISO standard 594. Similarly, the configurations of male luer 303 at the base of needleless access connector 300, in some embodiments, meets ISO standard 594. Collapsible valve 304 is disposed within housing 301.

Figure 1B:
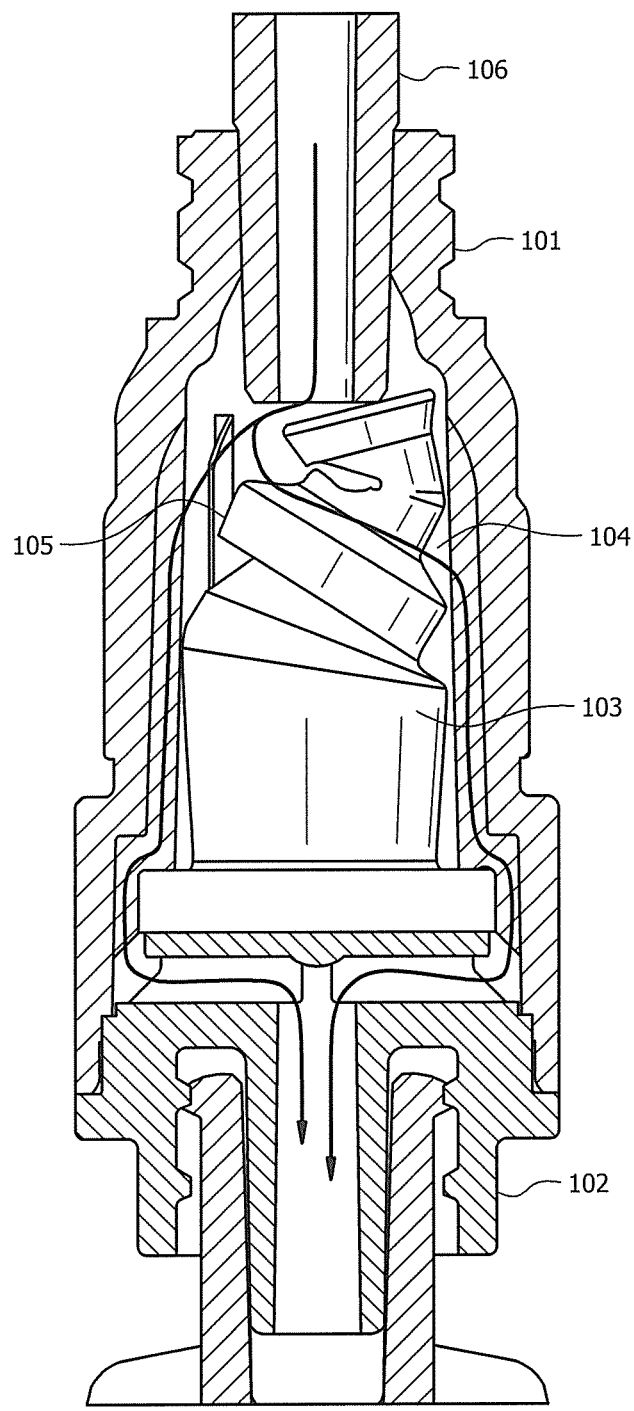

Collapsible valve 304 may be made of elastic material such as silicone rubber, which is deformable and biocompatible. Because collapsible valve 304 is made of deformable material, it will collapse when sufficient force is applied to it. Collapsible valve 304 includes first portion 304A, which is disposed within top threaded part 302 when valve 304 is in its uncollapsed state as depicted in FIG. 3A. First portion 304A may be substantially cylindrical in shape and may contain deviations from this cylindrical shape such as smiley cut 304B. Collapsible valve 304 also includes second portion 304C which is disposed in cavity 305 of housing 301. Unlike the prior art as depicted in FIG. 1, second portion 304C is devoid of duckbills or any other such deviations from its general shape, i.e., portion 304C's outside surface is annular. As such, in one embodiment, second portion 304C is cylindrical and has diameter d2 being greater than diameter d1 of first portion 304A. Collapsible valve 304 may also include third portion 304D. Third portion 304D may have diameter d3 that is larger than second portion 304C's diameter, d2.

Figure 3B:
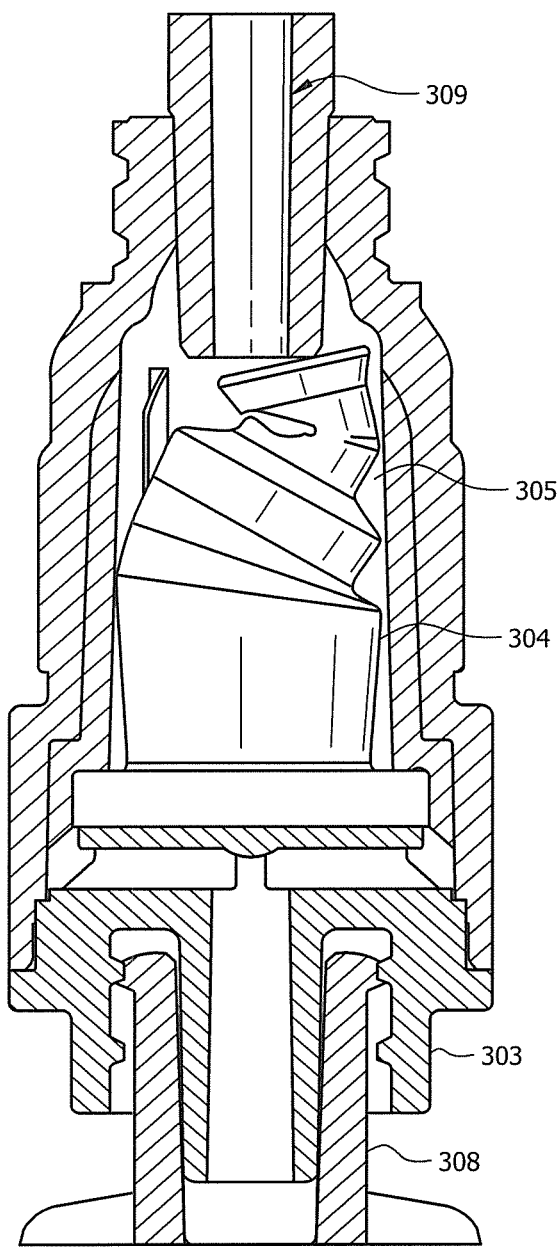

Collapsible valve 304 controls fluid flow through needleless access connector 200 and thereby provides a way of connecting devices to a catheter. In its uncollapsed state, as shown in FIG. 3A, collapsible valve 304 seals top threaded part 302. A further seal is provided at shoulder 307 by collapsible valve 304. When male luer 303 is connected to the catheter 308, in creating a seal at opening 306 and shoulder 307, collapsible valve 304 also seals catheter 308. To connect another device, such as an IV bag, to catheter 308, male luer 309 is inserted in opening 306 as shown in FIG. 3B. Collapsible valve 304 collapses as a result of the force imparted by male luer 309 and thereby allows fluid to flow from male luer 309 through needleless access connector 300, around valve 304 and into catheter 308, as shown in FIG. 3B.

Figure 4A:
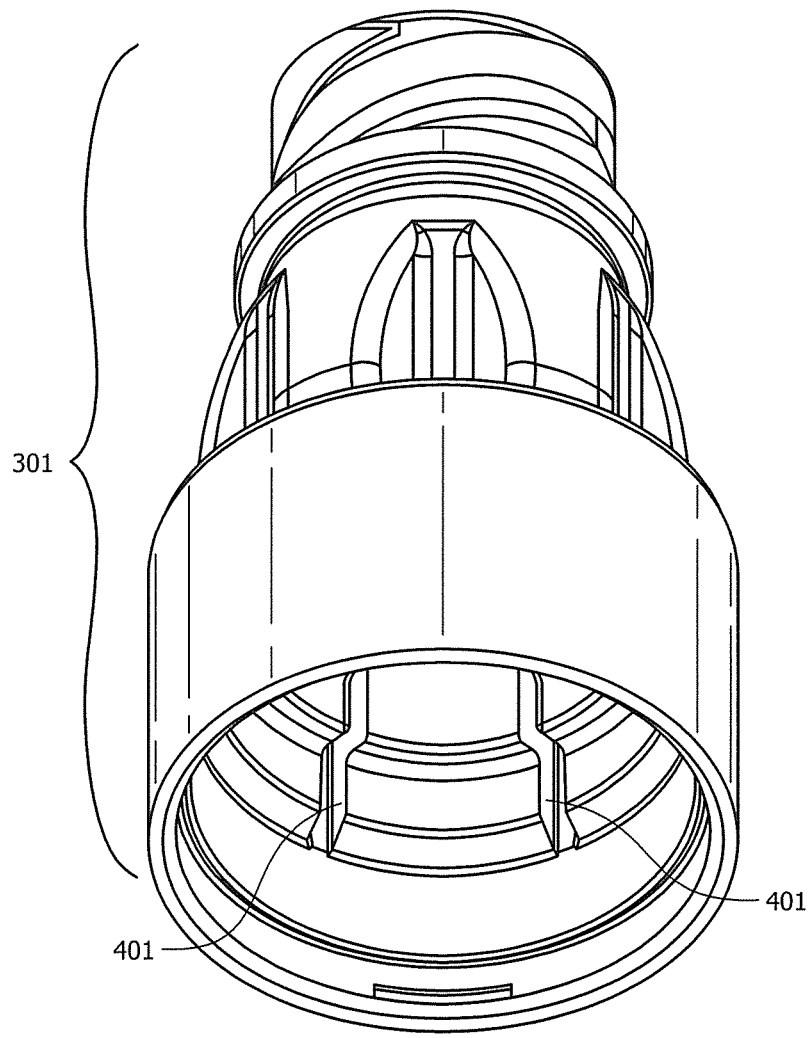
FIGS. 4A and 4B show flow channels in the housing of an exemplary needleless access connector according to one embodiment of the invention.
Figure 4B:
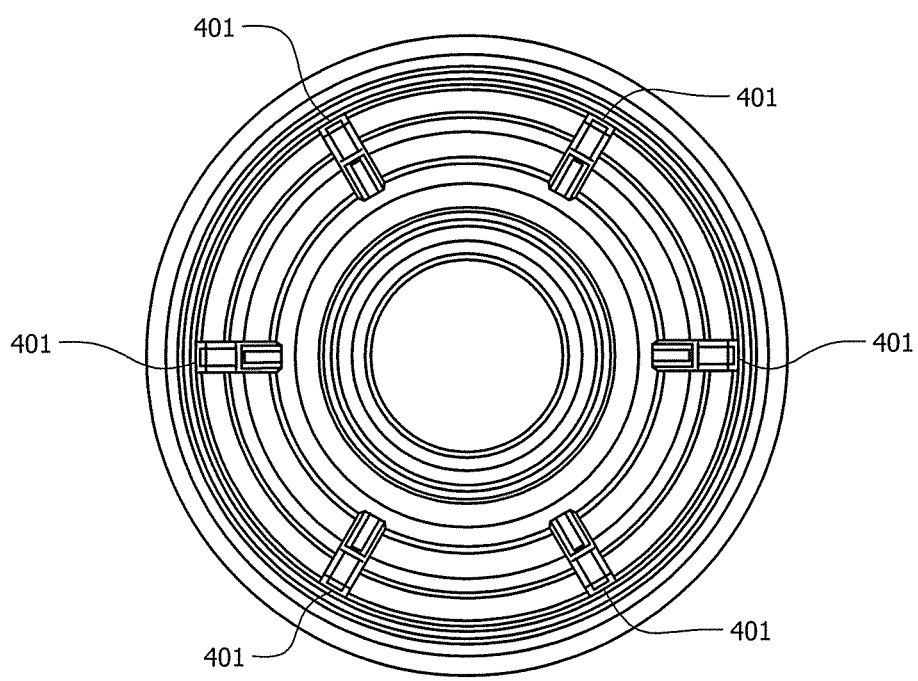

In some embodiments of the invention, housing 301 includes flow channels 401 as shown in FIGS. 4A and 4B. When collapsible valve 304 is in a collapsed state, flow channels 401 assist the flow of fluid around collapsible valve 304 and into the catheter. As indicated in FIG. 4A, flow channels 401 may be disposed in the upper portions of housing 401. FIGS. 4A and 4B show six flow channels 401 on the inside of housing 301, which promotes fluid flow. In some embodiments, the width of flow channel 401 is half the width of flow channels in typical needleless access connectors.

Figure 5A:
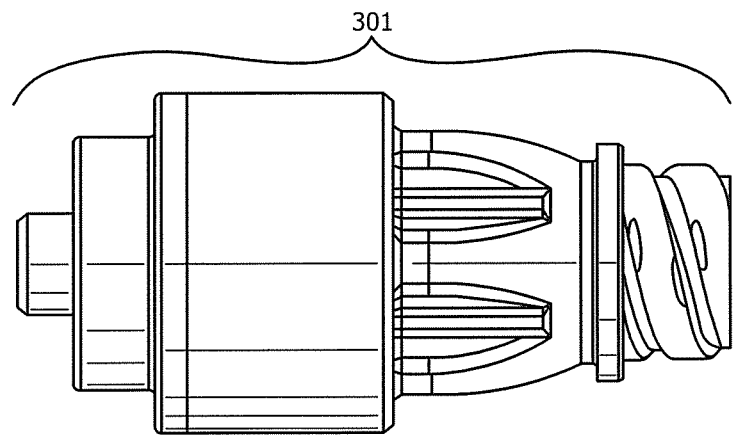
FIGS. 5A-5C illustrate different views of the housing of an exemplary needleless access connector according to one embodiment of the invention.
Figure 5B:
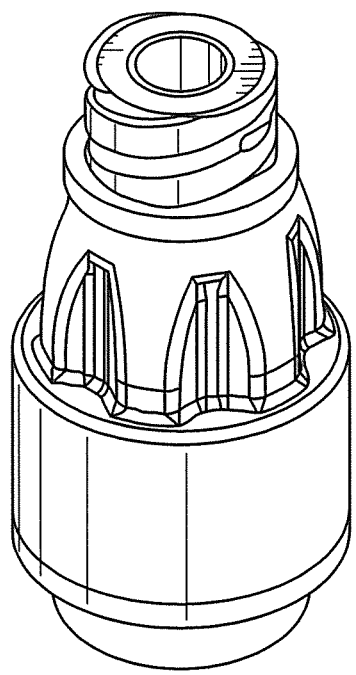
Figure 5C:
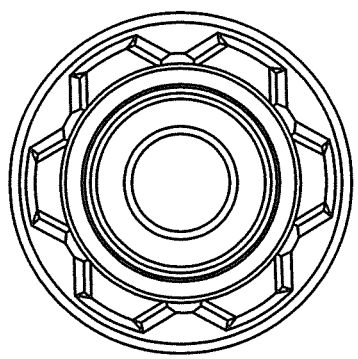

FIGS. 5A-5C show outside views of exemplary needleless access connectors according to one embodiment of the invention. It should be noted that the specific values given above are for exemplary embodiments and other embodiments may have somewhat different values. Other configurations with different sizes and shapes are within the scope of embodiments. In fact, any of a variety of positive displacement devices (and/or valves) can be adapted according to the concepts illustrated in the examples above.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A needleless access connector comprising:
   a housing; and
   a collapsible valve disposed in the housing, the collapsible valve having a first axial length of 0.62 to 0.82 inches and comprising:
      a first portion with at least one smiley cut in a section thereof and comprising a second axial length in the range of 0.22 to 0.28 inches; and
      a second portion coupled to the first portion, the second portion comprising a third axial length and an outside surface that is annular over the entire third axial length,
   wherein the collapsible valve is configured to provide positive displacement when actuated, and wherein the housing and collapsible valve are configured to provide positive displacement and a priming volume that is in the range of 0.17 to 0.19 milliliters.

2. The needleless access connector of claim 1, wherein the housing comprises:
   a male fitting at one end; and
   a female fitting at the other end.

3. The needleless access connector of claim 2, wherein the male and female fittings comprise luer fittings.

4. The needleless access connector of claim 1, wherein the housing is made from material selected from the list consisting of: polycarbonate, polystyrene and acrylonitrile butadiene styrene.

5. The needleless access connector of claim 1, wherein the housing comprises channels adapted to allow fluid to flow through them when the collapsible valve is collapsed.

6. The needleless access connector of claim 1, wherein the collapsible valve comprises elastic material.

7. The needleless access connector of claim 1, wherein the needleless access connector has a length of 1.02 to 1.13 inches.

8. The needleless access connector of claim 1, wherein the third axial length is 56% of the first axial length.

9. The needleless access connector of claim 1, wherein:
   the housing comprises an opening;
   the first portion comprises an end that, when the collapsible valve is in an uncollapsed state, is flush with the opening;
   the end of the first portion has a first diameter; and
   the outside surface of the second portion has a second diameter than is larger than the first diameter.

\* \* \* \* \*